United States Patent [19]

Bruls et al.

[11] 4,348,520

[45] Sep. 7, 1982

[54] METHOD FOR THE PREPARATION OF MELAMINE

[75] Inventors: Pierre G. M. B. Bruls, Born; Johannes G. van Hinsberg, Ulestraten; Rudolf van Hardeveld, Geleen; Dominique J. J. S. M. Moreau, Sittard, all of Netherlands

[73] Assignee: Stamicarbon, B.V., Geleen, Netherlands

[21] Appl. No.: 146,181

[22] Filed: May 2, 1980

[30] Foreign Application Priority Data

May 3, 1979 [NL] Netherlands ..................... 7903473

[51] Int. Cl.$^3$ ............................................. C07D 251/60
[52] U.S. Cl. ..................................................... 544/201
[58] Field of Search ........................................ 544/201

[56] References Cited

U.S. PATENT DOCUMENTS

| | | | |
|---|---|---|---|
| 3,700,672 | 10/1972 | Kokubo et al. | 544/201 |
| 3,723,430 | 3/1973 | Kokubo et al. | 544/201 |
| 3,895,007 | 7/1975 | Schwarzmann et al. | 544/201 |
| 4,109,090 | 8/1978 | van Hardeveld et al. | 544/201 |
| 4,156,080 | 5/1979 | van Hardeveld | 544/201 |

FOREIGN PATENT DOCUMENTS

| | | |
|---|---|---|
| 1187808 | 4/1970 | United Kingdom . |
| 1237780 | 6/1971 | United Kingdom . |
| 1282298 | 7/1972 | United Kingdom . |

OTHER PUBLICATIONS

Schwarzmann, *Hydrocarbon Processing*, Sep. 1969, pp. 184–186.

*Primary Examiner*—John M. Ford

[57] ABSTRACT

An improved method for the preparation of melamine by the conversion of urea and/or thermal decomposition products thereof. The urea and/or thermal decomposition products are converted to melamine in the presence of a gas mixture containing ammonia and carbon dioxide in a reaction zone containing a fluidized bed of catalytically active material. Melamine is desublimated from the melamine containing gas mixture in a desublimation zone by a dry-capture method leaving a desublimator off-gas mixture of ammonia, carbon dioxide and gaseous impurities. A major portion of this desublimator off-gas mixture is compressed and recirculated to the reaction zone as fluidizing gas for the bed of catalytically active material, without intervening treatment to remove gaseous impurities from the desublimator off-gas.

9 Claims, 1 Drawing Figure

METHOD FOR THE PREPARATION OF MELAMINE

BACKGROUND OF THE INVENTION

This invention relates to a method for the preparation of melamine by the conversion of urea and/or thermal decompositions products thereof in a fluidized bed of catalytically active material in the presence of a gas mixture containing ammonia and carbon dioxide.

One known process for the preparation of melamine at atmospheric pressure is described in *Hydrocarbon Processing*, September 1969 at pages 184–186. In that process, urea is reacted in a fluidized bed reactor in the presence of ammonia and carbon dioxide to form melamine. The melamine is recovered from the reaction gases by a "dry-catch" method using cooled gases to lower the temperature below the sublimation point of melamine. The off-gases leaving the desublimation step, freed of melamine and consisting mainly of ammonia and carbon dioxide, are partly recycled for use as fluidizing gas in the fluid bed reactor. However, prior to being recycled to the reactor, the off-gases are first subjected to a washing or scrubbing step with liquid urea, which scrubbing step is apparently there necessary to prevent an accumulation of impurities in the recirculated fluidizing gas.

During the scrubbing step, however, the urea is heated by the hot desublimator off-gases. In order to prevent undesirable side reactions, the temperature of the liquid urea must not be maintained at too high a level. Therefore a large amount of heat must be removed from the liquid urea at a relatively low temperature level in a liquid urea cooler, using cooling water.

Additionally, in such a urea scrubbing step, a portion of the liquid urea is entrained in the scrubbed off-gas mixture in the form of droplets, which cause clogging of downstream lines and equipment. These entrained urea droplets must therefore be removed from the off-gas mixture in a mist separator, or the like, which itself increases operating and maintenance requirements, and presents a risk of greater operating difficulties such as incrustation.

It is an objective of the present invention to provide an improved process for the preparation of melamine wherein the manner of recycling the desublimation off-gas mixture to the reactor is simplified. It is a further objective of this invention to provide an improved method for the preparation of melamine wherein the aforementioned difficulties encountered in the urea scrubbing step are eliminated.

BRIEF DESCRIPTION OF THE INVENTION

These and other objectives are accomplished according to the present invention by recirculating a major portion of the desublimation off-gas mixture, containing ammonia, carbon dioxide and gaseous impurities, to the reactor as fluidizing gas without any intervening treatment to remove the gaseous impurities therefrom. Applicant has surprisingly found, contrary to known processes, that the off-gas mixture resulting from a dry-capture melamine desublimation step can be directly utilized as fluidizing gas in the reactor, omitting any intervening step to remove gaseous impurities, without creating an accumulation of impurities in the circulating gas mixture, and without sacrifice to the purity of the melamine product obtained.

The impurities contained in the desublimator off-gas mixture typically include deamination products formed in the conversion of urea to melamine such as melam, melem, melon, ammeline and ammelide. To the extent that these impurities are present in the desublimator off-gas mixture, it has been found that they can simply be passed into the reactor, together with the ammonia and carbon dioxide, wherein they are either converted into melamine or to ammonia and carbon dioxide.

In a preferred embodiment of the process of the present invention, the partial pressure of ammonia in the fluid bed of catalytically active material in the reaction zone is maintained at a level of over 70 kPa, preferably at a level of over 100 kPa. More preferably, this partial pressure of ammonia should be maintained in the range of between 350 to 2,500 kPa. It has been found that maintaining the partial pressure of ammonia in the catalyst bed at an elevated level, that is, more than 70 kPa, the formation of impurities such as melam, melem, melon, ammeline and ammelide can be substantially reduced or eliminated, thus even more so rendering the subsequent purification steps of the known processes superfluous. As a practical matter, however, the pressure should not be so high as to make expensive equipment necessary. Therefore, the total pressure in the fluidized bed is preferably not over 2,500 kPa, and most preferably not over 1,500 kPa.

The conversion of urea into melamine in the presence of ammonia and carbon dioxide in a fluidized bed of catalytically active material can be effected by methods known in the art such as, for instance, the processes disclosed in U.S. Pat. No. 4,156,080. Any one of a number of known catalysts can be used in the fluidized bed of the reactor, such as aluminum oxide, aluminum oxide on silicon, silicon oxide, titanium oxide, zierconium oxide, boron phosphate or aluminum phosphate, or a mixture of two or more of these catalysts. The term catalyst or catalytically active material as used herein shall be understood to mean any material promoting, under the reaction conditions applied, the conversion of urea into melamine.

The temperature in the fluidized bed in which the conversion of melamine to urea takes place will generally be in the range of between about 325° C. and 460° C. However reaction temperatures between about 370° and 400° C. are particularly preferred. The ideal temperature to be applied depends, in part, upon the total pressure in the reactor (higher temperatures being used at higher pressures).

The separation of melamine from the reaction gases coming from the reactor can be effected by either direct or indirect cooling. For instance, direct cooling can be accomplished by contacting the reaction gas mixture with cold ammonia gas or cooled mixtures of ammonia and carbon dioxide gases.

Another method for the desublimation of melamine from the reaction gas mixture is to introduce the gas mixture into one or more fluidized beds of melamine particles, which fluidized beds are indirectly cooled, preferably by means of cooling water in heat exchange tubes located throughout the fluidized bed of melamine particles. By running the cooling water through the heat exchange tubes counter-current to the direction of flow of the reaction gas mixture, high quality steam can be formed (i.e. steam of high pressure and temperature).

A further advantage of indirect cooling via a fluidized bed of melamine is that relatively large melamine particles are obtained having a relatively narrow particle size distribution. The melamine obtained in this mamnner is free-flowing, and can be conveyed in bulk. By comparison, where direct cooling is used, the melamine produced has an extremely fine particle size, which may give difficulties in flow and bulk handling characteristics.

The temperature in the desublimation step or zone is preferably between about 180° and 250° C. The pressure at which the desublimation of melamine is effected will generally be a little lower than the pressure prevailing in the reactor or reaction zone, as a result of loss of pressure in the various lines and equipment. As the desublimation step is generally carried out at above atmospheric pressures, specialized equipment is necessary to remove the melamine powder from the desublimation equipment. This can be accomplished, for instance, utilizing a cyclone or a rotating valve.

The method of the present invention has the advantage that relatively little equipment is necessary, while the consumption of energy is substantially lower, as compared to the known method. Thus it is possible, according to a preferred embodiment, to convert the heat content of the reaction gases, and specifically the heat of desublimation of the melamine contained therein as well as the sensible heat of the reaction gases, directly into high quality steam.

Moreover, maximum efficient use can be made of the heat content of the desublimation off-gas mixture in the conversion of urea into melamine, in that this off-gas mixture can be passed directly, without purification or loss of heat, into the melamine reactor. Under the known method, on the other hand, the heat content of this off-gas mixture is in large part taken up by the liquid urea used in scrubbing, which in turn is discharged into cooling water at such a low temperature that it is of little or no value in other processing operations.

If the desublimation off-gas mixture is compressed to compensate for the loss of pressure through the reactor and desublimator, a heat exchange is preferably carried out between this off-gas before and after compression. In this manner, any extremely fine melamine particles, which may not be caught in the dust catching cyclone of the desublimation step, and which are still present in the desublimation off-gas mixture, will be sublimated by the heat transfer so that little or no solid particulate dust will enter the compressor. This has the advantage of reducing wear on the compressor that would occur if dust is allowed to enter into the compressor.

If the desublimator off-gas mixture also contains catalyst dust, in addition to the fine melamine dust, it is desirable to filter the gas, preferably after the above noted heat exchange step, but in any event prior to compression.

Under the improvement of this invention, 50 to 90% of the desublimator off-gas mixture is recirculated to the reactor and utilized as fluidizing gas. A portion of the desublimator off-gas mixture must be removed from the process because the conversion of urea into melamine releases six molecules of ammonia and three molecules of carbon dioxide per molecule of melamine formed. In general, from about 10 to 40% of the desublimator off-gas mixture will be removed from the process. This removed off-gas mixture can be effectively processed by various methods which either utilize it as a mixture, or separate out the valuable constituents, particularly the ammonia. For instance, it is possible to absorb the excess desublimation off-gas mixture, which primarily consists of ammonia and carbon dioxide in a molecular ratio of 2:1, into water or into an aqueous solution, and, possibly after concentration, to feed the resulting solution as a carbamate feed into a urea synthesis reactor. Other possibilities include compression of the gas mixture to urea synthesis pressure, or processing the off-gas mixture into an ammonia-containing fertilizer.

Finally, it is also possible to separate the gas mixture into its component parts by means of an ammonia-carbon dioxide separation process such as disclosed in British Patent Specification No. 1,129,939, U.S. Pat. No. 4,163,648 or U.S. Pat. No. 4,013,431.

DETAILED DESCRIPTION OF A PREFERRED EMBODIMENT

Figure 1:
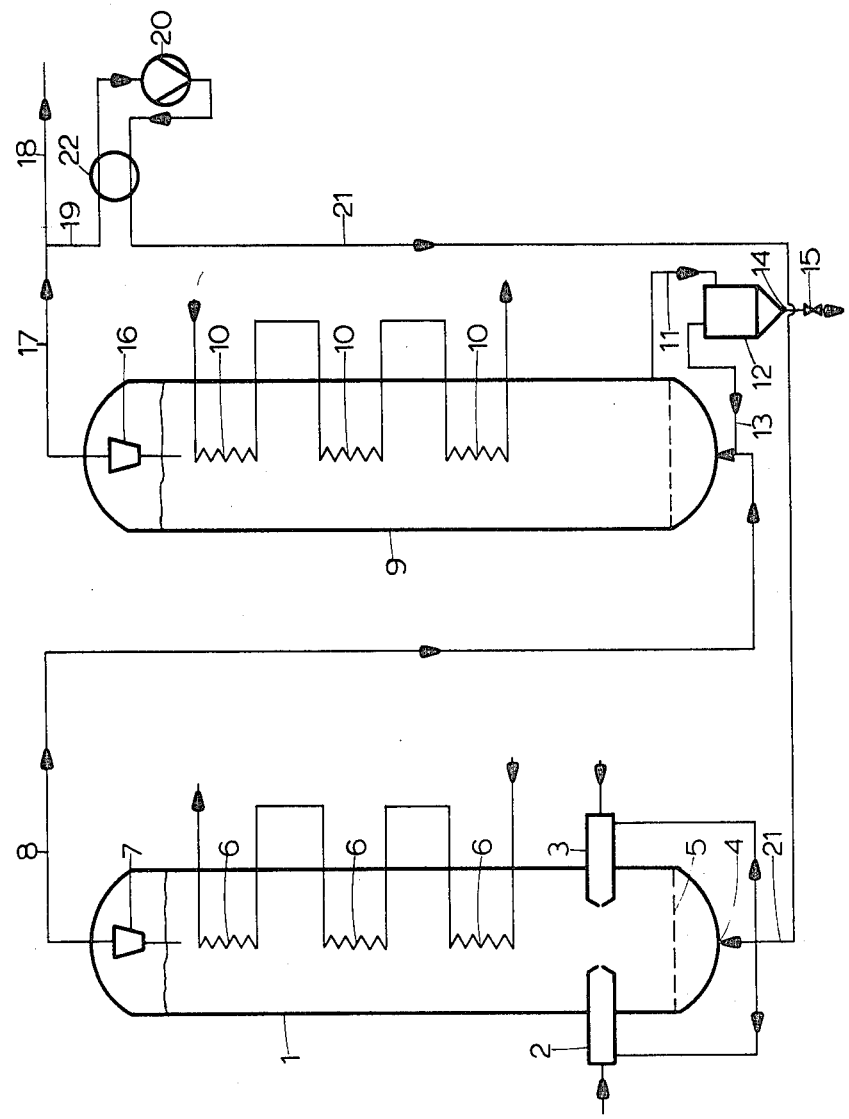

The FIGURE diagrammatically depicts one embodiment of a melamine from urea process in which the improvement of the present invention may be applied.

Urea is atomized with the gas mixture supplied through line 21 and introduced through sprayers 2 and 3 into a fluidized bed of catalyst particles contained in reactor 1. This catalyst bed is fluidized by means of a gas mixture supplied through fluidizing gas supply line 4 and gas distributor plate 5. The desired temperature is maintained in the fluidized bed by means of heat exchange pipes 6, which have been shown here diagrammatically. The melamine-containing reaction gas mixture flows through cyclone 7, to remove entrained catalyst fines, and is fed from the reactor via line 8 to desublimator 9. Desublimator 9 contains one or more beds of fluidized melamine particles in which the melamine contained in the reaction gas mixture is desublimated and separated from the remaining off-gas. The heat released by this desublimation is removed through heat exchange tubes 10 in which cooling water is converted into high pressure steam.

Solid melamine particles are removed from the bottom of desublimator 9 through line 11, and separated in separator 12 from the remaining gases. The remaining gases are returned to desublimator 9 through line 13. Melamine product is removed from the process via line 14 and pressure reduction valve 15. The desublimator off-gas mixture is freed of melamine in cyclone 16 and removed from the desublimator via line 17.

A portion of this desublimator off-gas mixture is recirculated via lines 17, 19 and 21, to reactor 1 wherein it is introduced as a fluidizing and atomizing gas. Prior to being brought up to the reactor pressure in compressor 20, the off-gas is heated with compressed off-gas in heat exchanger 22 in order to sublimate any melamine dust that might remain in the desublimator off-gas mixture. The remaining part of the desublimator off-gas mixture, that is not recirculated, is removed from the process through line 18 to another processing facility for, e.g., urea synthesis, ammonia-carbon dioxide separation, or fertilizer preparation.

A preferred embodiment of the invention will be described in the following example, which is for illustrative purposes only.

EXAMPLE

Melamine preparation was carried out in an installation as described in the FIGURE. The melamine reactor was fed with 20,000 kg of urea and 30,000 kg of gaseous ammonia and carbon dioxide per hour. The reactor was operated at a temperature of 375° C., a total pressure of 1,000 kPa. The partial pressure of ammonia was maintained at 600 kPa.

The melamine containing reaction gas mixture was fed from the reactor to desublimator 9, which contained a fluidized bed of melamine particles. About 7,000 kg of melamine product per hour was discharged from the desublimator. The resulting melamine product had good free-flowing properties and a purity of 99.9% without the need for further purification or processing.

Eighty percent of the desublimator off-gas mixture, substantially free of melamine, was recirculated to the melamine reactor as fludizing gas after compression to compensate for the pressure reduction across the reactor and desublimator. Prior to compression, the desublimator off-gas mixture was heated with compressed off-gas in a heat exchanger to sublimate any remaining melamine dust. The remaining 20% of the desublimator off-gas mixture was fed to an ammonia-carbon dioxide separation facility.

What is claimed is:

1. In a method for the preparation of melamine comprising:
   a reaction zone wherein melamine is formed by the conversion of urea and/or thermal decomposition products thereof in a fluidized bed of catalytically active material in the presence of a gas mixture containing ammonia and carbon dioxide, and
   a desublimation zone wherein said melamine is desublimated from a melamine containing gas mixture by a dry-capture method leaving a desublimator off-gas mixture containing ammonia, carbon dioxide and gaseous impurities,
the improvement wherein at least a major portion of said desublimator off-gas mixture is compressed and recirculated to said reaction zone as fluidizing gas for the bed of catalytically active material, without intervening treatment to remove said gaseous impurities.

2. The method of claim 1 wherein said desublimator off-gas mixture, prior to being compressed, is heated by indirect heat exchange with said compressed desublimator off-gas mixture.

3. The method of claim 1 or 2 wherein said desublimator off-gas mixture is filtered prior to being compressed to remove entrained solid particles.

4. The method of claim 1 wherein 50 to 90% of said desublimator off-gas mixture is recirculated to said reaction zone.

5. The method of claim 1 wherein said desublimation zone contains at least one fluidized bed of melamine particles.

6. The method of claim 5 wherein at least one fluidized bed of melamine particles is indirectly cooled by means of cooling water, which cooling water is thereby converted to process steam.

7. The process of claim 6 wherein said cooling water is recirculated through heat exchange tubes in said desublimation zone in a direction generally counter-current to the direction of flow of said melamine containing gas mixture in said desublimation zone.

8. The method of claim 1 wherein the partial pressure of ammonia in the gas mixture in said fluidized bed of catalytically active material in the reaction zone is over 100 kPa.

9. The method of claim 8 wherein said partial pressure of ammonia is between 350 and 2,500 kPa.

* * * * *